(12) United States Patent
Götte

(10) Patent No.: US 9,271,815 B2
(45) Date of Patent: Mar. 1, 2016

(54) DEVICE FOR THE PREVENTATIVE AND ACUTE TREATMENT OF TEETH AND GUMS

(76) Inventor: Dieter Götte, Wiesbaden (DE)

( * ) Notice: Subject to any disclaimer, the term of this patent is extended or adjusted under 35 U.S.C. 154(b) by 0 days.

(21) Appl. No.: 13/811,449

(22) PCT Filed: Jul. 15, 2011

(86) PCT No.: PCT/EP2011/062149
§ 371 (c)(1),
(2), (4) Date: Jan. 22, 2013

(87) PCT Pub. No.: WO2012/013522
PCT Pub. Date: Feb. 2, 2012

(65) Prior Publication Data
US 2013/0122460 A1 May 16, 2013

(30) Foreign Application Priority Data
Jul. 29, 2010 (DE) ............... 20 2010 010 800 U

(51) Int. Cl.
*A61C 17/00* (2006.01)
*A46B 7/04* (2006.01)
*A46B 7/08* (2006.01)
*A46B 9/00* (2006.01)

(52) U.S. Cl.
CPC ............... *A61C 17/005* (2013.01); *A46B 7/04* (2013.01); *A46B 7/08* (2013.01); *A46B 9/005* (2013.01); *A46B 2200/1066* (2013.01)

(58) Field of Classification Search
CPC .......... A61C 17/005; A46B 7/04; A46B 7/08; A46B 9/005
USPC ........... 433/141, 118, 124, 126, 82; 15/167.1; 401/268
See application file for complete search history.

(56) References Cited

U.S. PATENT DOCUMENTS

| 2,653,598 A | * | 9/1953 | Torino | 601/141 |
| 3,818,911 A | * | 6/1974 | Fournier | 604/1 |
| 5,044,356 A | * | 9/1991 | Fishman et al. | 601/142 |
| 5,078,754 A | * | 1/1992 | Jefferies et al. | 51/298 |
| 5,176,754 A | * | 1/1993 | Hirzel | 118/258 |
| 5,283,924 A | * | 2/1994 | Kaminski et al. | 15/244.1 |
| 5,774,925 A | | 7/1998 | Pryor, III | |
| 6,471,300 B1 | | 10/2002 | Tomiyama | |

FOREIGN PATENT DOCUMENTS

| CN | 2060305 U | 8/1990 |
| CN | 1062457 A | 7/1992 |

(Continued)

OTHER PUBLICATIONS

Machine Translation of WO/00/48484 Peter Ulrich. Aug. 24, 2000.*

*Primary Examiner* — Ralph Lewis
(74) *Attorney, Agent, or Firm* — Paul & Paul

(57) ABSTRACT

A device is provided for preventative and acute treatment of teeth and gums, with a handle (1) and a treatment element mounted on the handle for insertion into the mouth of a patient, comprising an axis of rotation perpendicular to the longitudinal direction of the handle. In order to treat teeth and gums, for example, for dissolving and removing lipophilic bacteria, and to provide for treatment and massage of the gums without risk of damage to the epithelia, in addition to feeding care and treatment agents, the treatment element (2) comprises a three-dimensional, rotationally symmetrical surface made at least partially of open-pore foam, wherein the treatment element (3) is mounted so as to be freely rotatable about the axis of rotation, such that the rotationally symmetrical surface thereof can be rolled along the teeth and/or gums.

15 Claims, 1 Drawing Sheet

(56) References Cited

FOREIGN PATENT DOCUMENTS

| | | |
|---|---|---|
| CN | 2365950 Y | 3/2000 |
| CN | 2648894 Y | 10/2004 |
| EP | 1004282 A2 | 5/2000 |
| FR | 2621792 A1 | 4/1989 |
| JP | 2003 319834 A | 11/2003 |
| WO | 00 48484 A2 | 8/2000 |
| WO | 2004 004515 A1 | 1/2004 |

* cited by examiner

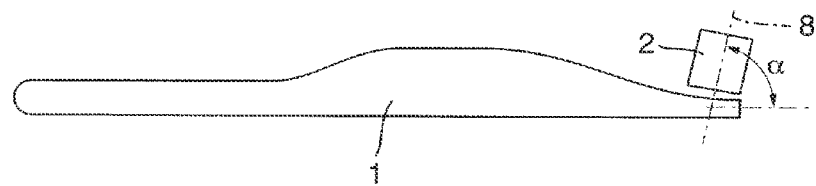
Fig. 1
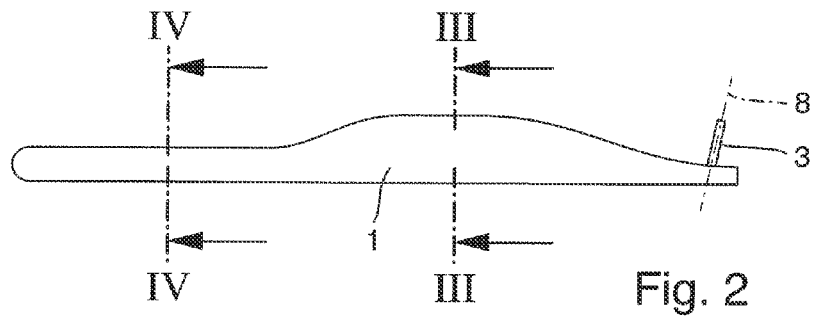
Fig. 2
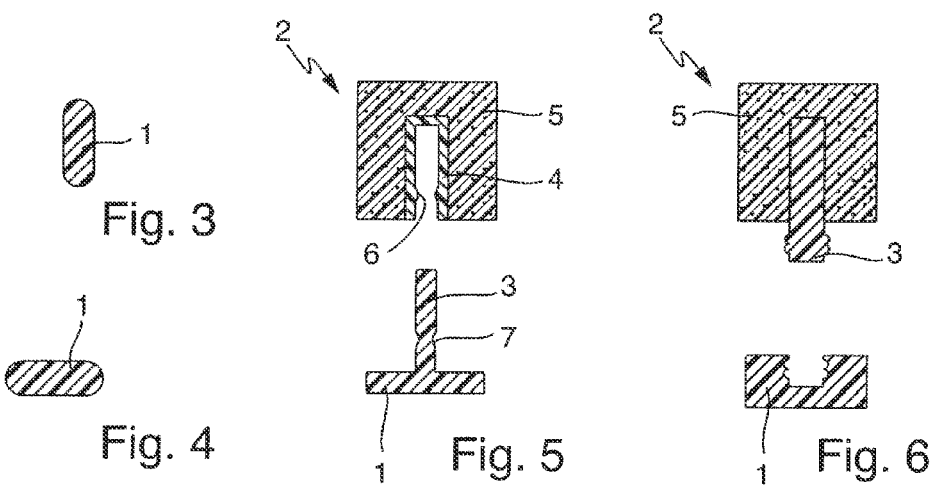
Fig. 3
Fig. 4
Fig. 5
Fig. 6

DEVICE FOR THE PREVENTATIVE AND ACUTE TREATMENT OF TEETH AND GUMS

The present invention concerns a device for the preventative and acute treatment of teeth and gums comprising a handle and a treatment element which is mounted to the handle and which is to be inserted into the mouth of a patient and which has an axis of rotation extending approximately perpendicularly to the longitudinal direction of the handle. Devices for the preventative acute treatment of teeth or gums have already long been known in the state of the art in the form of toothbrushes. In particular electric toothbrushes with rotating bristle heads are also known, in which the axis of the bristle head extends substantially perpendicularly to the longitudinal direction of a corresponding handle.

Such toothbrushes, irrespective of their configuration, are however only limitedly suitable specifically for the prophylaxis and therapy of parodontosis or parodontitis, even if numerous attempts have already been made in also aiming at more gently and more carefully treating gums and providing for massage thereof specifically by adaptation of the outer bristles of toothbrushes.

Parodontitis (synonym: gum inflammation) is a bacterially induced inflammation which involves substantially irreversible destruction of the tooth holding apparatus (paradontium, peridontium), with the consequence of loosening of teeth and ultimately tooth loss. Inflammation of the gums (gingivitis) is the initial disease and parodontitis is the consequential disease. The chronic state of disease is referred to as parodontosis (synonym: alveolar atrophy). The economic significance of parodontitis/parodontosis is clear from the fact that, as from the 40th year of life more teeth are lost due to parodontosis than caries. The frequency of the precursor disease gingivitis is stated as being 100% of the population. The corresponding data for parodontitis frequency of the remaining bite are 35% among 20-year olds and 70% in those over 50. 4-8% of adults and between 14-22% of senior citizens have a severe degree of parodontitis. It is to be assumed that at present around 23 millions of people in Germany have a parodontal need for care with differing urgency for therapy.

In the case of parodontitis as an acutely inflammable form of parodontosis, a distinction is drawn between 2 forms: the "apical" form (extending from the tip of the tooth root) and the "marginal" form (starting from the gingival margin). The two forms however can merge into each other.

Parodontitis is triggered by bacterial plaque (tooth coating), a biofilm which adheres tenaciously to the tooth, which usually occurs with the following pattern:
  coating of the clean tooth with saliva glycosides,
  adhesion of microorganisms from the saliva to that layer,
  establishment of a primary flora,
  development of selective flora and plaque maturing, and
  dominance of gram-negative bacteria and beginning of a chronically inflammatory process.

The plaque hardens under the influence of the saliva at the gingival edge and there leads to mechanical irritation. The tooth coating acquires a pathophysiological significance inter alia only because a biofilm which can no longer be peeled off is in direct permanent contact with the gingival edge. Biofilm mineralisation leads at the surface to fresh layers of vital plaque and, because of the porous structure of the tartar, the retention of toxic substances. The plaque bacteria produce exotoxins which diffuse into the adjoining gums and there cause an inflammation process with reddening and swelling. Further cytotoxic substances are butyrate, propionate and ammonium. Gum inflammation (gingivitis) occurs, which is still reversible after professional teeth cleaning.

Based on the fact that chronic and progressive inflammation of the inner marginal epithelium or—in later stages of the infection—the gum pockets are the main triggers of parodontitis, outstanding significance for keeping the tooth holding apparatus healthy is attributed to the care of that anatomical structure. Even in the case of healthy people micro-injuries to the marginal epithelium which in turn form the starting point for bacterial colonisation and plaque production frequently occur due to incorrect techniques in cleaning the teeth like an excessively high pressure applied by the brush, the choice of an excessively hard brush or an excessively hard setting of the water jet of an oral water jet device.

Other aids for cleaning teeth like the individual use of dental floss or inter-dental brushes for cleaning the spaces between teeth afford advantages in conscientious and regular use but do not in any way replace professional tooth cleaning by the dentist or people trained in dentistry.

In the anatomically constricted oral cavity only a second person can gain a good visual impression of the amount of plaque by means of special instruments, at locations which involve poor anatomical access, with the availability of special instruments like for example ultrasound cleaning devices or other dental instruments.

In regard to the correct technique for cleaning teeth using toothpaste or tooth salt there are two preferred techniques: 1. Cleaning movement from "red" towards "white", that is to say the bristles of the toothbrush head are always moved only from the gum ("red") towards the crown of the tooth ("white"), or 2. "Circulatory" movements of the brush head, by means of which the tooth is to be brushed and the gingival margin is to be gently massaged. Which of the two techniques is actually the optimum one if not unambiguously settled from the scientific point of view. What is beyond dispute however is that cleaning teeth and in particular removing the plaque with the brush are performed too rarely and often with a defective technique and involving an inadequate period of time. Conventional tooth cleaning with brush and toothpaste does not resolve the problem of inflammation of the marginal epithelium and therefore urgently needs to be supplemented by an approach which causally addresses the particular problems of chronic parodontitis.

The known toothbrushes and other devices for the preventative treatment of teeth and gums are accordingly not suitable or are only limitedly suitable for preventing parodontosis or stopping the advance thereof. Rather, for the treatment and prevention of parodontosis it is necessary to care for teeth and gums with a treatment means which is also suitable for dissolving and removing lipophilic bacteria and to provide a corresponding device which besides the supply of suitable care and treatment agent also permits even more gentle and careful treatment and massage of the gums without any risk of damaging the marginal epithelium.

That object is attained in that the treatment element has a three-dimensional, rotationally symmetrical treatment surface which at least partially comprises an open-pore foam, wherein the treatment element is supported freely rotatably about the axis of rotation in such a way that it can be rolled with its rotationally symmetrical surface in the mouth of the patient along the teeth and/or gums thereof.

Unlike conventional devices for the treatment of parodontitis or parodontosis the present invention does not have any bristles, projections or the like which could damage the gums. Admittedly, plastic or foam elements are also already known in the state of the art, which can be moved for example directly over gums and teeth by being fitted on to the fingertips, but even the friction produced in that way can cause damage to the gums and the gaps between the teeth are also poorly reached in that way.

The present invention in contrast provides a treatment element which on the one hand comprises an open-pore foam which is easily deformable and which can be very well adapted to other surfaces while on the other hand the treatment element, by virtue of its three-dimensional rotationally symmetrical treatment surface can easily roll against the gum and/or or the teeth, in which case considerably less friction is produced between the treatment element and the gum, than is possible with other known devices. Unlike for example rotating bristle heads which are driven by a corresponding motor and which are oriented with their axis perpendicularly to the surface of the tooth or gum the treatment element in the present case is freely rotatable and thus can easily roll against the surface of the gum or teeth by suitable movement and orientation of the axis parallel to the surface of the gum or teeth. During the treatment therefore the orientation of the axis of rotation is precisely perpendicular to the orientation which must be set when involving treatment with a rotating toothbrush.

The invention comprises a device which is toothbrush-like in its basic structure (see FIGS. 1 and 2) which instead of the brush head carries on a carrier a soft, rotatable and replaceable sponge which fits on a plastic capsule and can receive cleaning oil or other cleaning and caring substances. Like a toothbrush the device is introduced into the oral cavity and the sponge is guided with a gentle pressure at the inside and the outside along the tooth enamel/gingival boundary. That is intended to provide for massage of the marginal or connecting epithelium and wetting of that anatomical structure with for example tooth oil or other care substances. When performing the movement, this does not involve any "friction" between sponge and gum as the soft sponge which is matched to the anatomy can rotate freely and easily moveably on the axis member. The patient himself determines the pressure with which the sponge comes into contact with the gum. The device permits gentle and careful massage of the gum and the marginal epithelium in so far as the rotationally symmetrical treatment element is simply guided under a light pressure along the inside and outside of the tooth/gingival boundary. In that way gum and marginal epithelium are gently massaged and cleaned.

The open-pore foam finally makes it possible for the treatment element to be impregnated with a treatment fluid which is delivered to the gum during the rolling movement. In particular oils and the like can be used for that purpose, which are capable of absorbing and removing fat-soluble toxins which are produced by various oral bacteria, and that is usually not successfully achieved with toothbrush and toothpaste.

The present invention is admittedly not intended to replace conventional toothbrushes but rather is intended to serve and be used as an addition specifically for the treatment of parodontitis and for the prevention of parodontosis. It will be appreciated however that accordingly when using toothbrushes the gums are to be treated as kindly as possible (for example by using soft bristles or the like), and they can be then treated separately and additionally with the device according to the invention.

A further area of use of the invention is the care of tooth-bearing or prosthesis-bearing jaw implants. In general those implants heal nicely after surgical involvement. However entry points for pathogens which can potentially lead to infections always occur at the contact surfaces relating to the surrounding tissue. Good care of the implants is therefore an indispensable prerequisite for permanent success of this surgical measure which is becoming more and more important. Cleaning with the conventional toothbrush is often not sufficiently gentle because of excessively hard or excessively short bristles and when the wrong cleaning technique is used even leads to damage to the sensitive mucous membrane at the mucous membrane/implant boundary. The invention can contribute to being able to better care for the implants which have healed in place and reducing the bacterial toxin loading of the tissue immediately surrounding the implant.

Further features of the device according to the invention are to be found in the appendant claims which are discussed in greater detail hereinafter. As already mentioned the treatment system has a three-dimensional rotationally symmetrical surface. These include the surfaces of numerous rotational bodies including balls, ellipsoids, cones, cylinders, etc., wherein for practical reasons the shape of a cylindrical surface or a peripheral surface of a cylinder is preferred for the treatment element. The treatment element can be for example a cylindrical foam body, into the one end of which is inserted a firmer plastic element which imparts the required stability to the treatment element for rotatable connection to the handle. It will be appreciated that the treatment surface itself in that case comprises the open-pore soft foam which is in the shape of cylinder or a hollow cylinder and whose treatment surface is formed by a cylindrical surface. The diameter of such a treatment surface can be in a range of between 5 and 20 mm but should preferably be between 8 and 15 mm.

It will be appreciated that the shape can also differ slightly from a cylindrical shape, for example the treatment element could also be in the form of a truncated cone or a kind of barrel shape, that is to say it can be of a somewhat convex shape. In that case the foregoing diameter specifications relate to the mean value of such an element, as measured over the axial length.

The diameter should not be excessively small as the treatment element must have an inner firmer core for freely rotatable connection to the handle and the foam of the treatment surface should not be excessively thin in order on the one hand to be able to absorb sufficient treatment fluid but on the other hand to also protect the gum from pressure contact with the inner firmer core or to adequately cushion it.

In an embodiment the treatment element can have an inner plastic sleeve which is stable in respect of shape and which can be fitted with as little friction as possible but in accurately fitting relationship on to a suitable axis member which extends at one end of the handle and approximately perpendicularly thereto.

It is however also possible for a corresponding fitment axis member to be fixedly connected to the foam which forms the treatment surface, and to be provided on the side towards the handle with a projecting connecting portion which can be fitted in accurate fitting relationship into a mounting bush in the handle. In that case either the connecting portion could be mounted rotatably in the bush or however the connecting portion is non-rotatably latched to the bush, in which case the bush in turn is easily rotatable in a suitable mounting.

The above-described variants make it possible for the treatment element to be replaced at any time and for the corresponding handle to be used afresh. In both cases however it is desirable if the plastic sleeve and the associated axis member or the connecting portion and/or the bush have latching elements so that the treatment element which on the one hand is still to remain freely rotatable is however axially fixed with respect to the handle so that the treatment element cannot become unintentionally loose during a treatment.

The open-pore foam layer arranged around the axis of the plastic sleeve should be of a thickness of at least 1 mm, preferably a thickness of at least 2 mm. The maximum thickness of the foam layer is defined by the maximum diameter or radius of the treatment element, from which the radius of the central spindle or sleeve is also to be subtracted. In practice therefore the maximum thickness of the foam layer should not exceed a value of between 5 and 10 mm. As already mentioned the thickness of that foam layer serves on the one hand for absorption capability for treatment fluid, but on the other hand also for cushioning the axis member or plastic sleeve in the interior of the treatment element. In addition the open-pore foam layer possibly accommodates a treatment fluid, in which respect it will be appreciated that this layer can accommodate correspondingly more treatment fluid, the thicker it is or the greater its total volume is.

The axial length of the treatment element is also adapted to the human anatomy and should therefore be between a minimum of 5 mm and a maximum of 20 mm, preferably between 8 and 15 mm.

To be able to optimally orient the treatment element in the mouth of a patient, in an embodiment the axis is angled with respect to the longitudinal direction of the handle through an angle differing somewhat from 90°, for example through 80° to 88°.

It will be appreciated that the foam of the treatment surface should comprise a permanently elastic material and should not be permanently deformed by being rolled against teeth and/or gums, but rather, during the rolling movement, on the one hand should very quickly adapt to the anatomical factors involved but thereafter should also immediately resume the original shape again.

The handle of the device according to the invention substantially corresponds to the handle of a toothbrush, in which respect the present invention differs from a toothbrush in particular in that, instead of the bristles, there is an axis member extending perpendicularly to the longitudinal extent of the handle, or a corresponding mounting bush, which define an axis of rotation, wherein the cross-section of the handle, at least in a portion which is typically gripped by thumb and index finger, is of a greater dimension in a direction parallel to that axis of rotation, than perpendicularly thereto. That self-evidently serves the purpose of being able to easily exert the required pressure between the rolling cylindrical surface or reduction surface and the teeth or gums. In the rest of the region the handle can correspond to the cross-section of usual toothbrushes.

The larger cross-section, provided in a central portion of the handle, in a direction parallel to the axis makes it possible to easily exert a corresponding force perpendicularly to the axis on the handle and thus also on the treatment element without the treatment element tilting. At the same time such a handle affords a simple possible way of establishing the orientation of the treatment element in the mouth solely on the basis of the handle. That is for example appropriate and desirable when a patient himself is not capable of correspondingly caring for his teeth, and that has to be done by a third person or a carer.

The mean pore size of the foam should be between about 0.1 and 1 mm, preferably between 0.2 and 0.5 mm. The pore size has on the one hand an influence on the stability in respect of shape and elasticity of the treatment element, but on the other hand it also influences the capability of absorbing and delivering treatment fluids. Excessively large pores under some circumstances have the result that the treatment fluid flows out of the treatment element very quickly, even if it was completely saturated therewith. A treatment fluid can be uniformly applied and distributed by correspondingly smaller pores.

Excessively small pores in contrast mean that the foam has a tendency to be stiffer and not sufficiently yielding in relation to teeth and gums so that the above-mentioned mean pore sizes represent preferred ranges which however may also depend on the specifically selected plastic material and can vary accordingly.

Further advantages, features and possible uses of the present invention will be clearly apparent from the description hereinafter of a preferred embodiment and the accompanying Figures in which:

FIG. 1 shows a side view of the device according to the invention,

FIG. 2 shows a view of the device according to the invention similarly to FIG. 1 but without the treatment element 2, FIG. 3 shows a cross-section through a handle of the device, FIG. 4 shows a view in section of the treatment element 2, FIG. 5 shows the associated fitment axis member 3, and FIG. 6 shows an alternative variant of the device according to the invention.

It will be appreciated that the device according to the invention is only diagrammatically shown in the accompanying Figures and a corresponding treatment device can actually differ markedly from the diagrammatically illustrated subject-matter in regard to the specific form, in particular in regard to ergonomic configurations.

FIG. 1 shows on the one hand a handle 1 which has similarities with the handle of a toothbrush, but with the exception of the cross-section III-III in the central region of the handle which is shown in FIG. 3 and which, in relation to the treatment element 2, is of a larger cross-sectional dimension parallel to the axis of the treatment element, than perpendicularly thereto. In the case of a toothbrush in which the treatment element 2 were replaced by a bristle head the cross-section would have a tendency to be wider transversely relative to the bristles than parallel thereto, that is to say precisely the reverse to the present case. The handle however has the cross-sectional shape of a toothbrush in the rear region, as shown in the cross-section IV-IV as shown in FIG. 4.

The treatment element 2 is a cylindrical foam body whose precise configuration will also be described with reference to FIG. 5.

FIG. 2 shows the handle 1 without treatment element 2 so that it is possible to see the fitment axis member 3 which extends from one end of the handle and approximately perpendicularly to the longitudinal direction thereof. The axis member 3 can be formed integrally with the handle 1 but can also be a pin which is cast or fitted separately into the handle 1. FIG. 3 shows the above-mentioned cross-section through the handle 1, corresponding to the section plane indicated at III-III in FIG. 2.

FIG. 5 in the lower part shows the front end portion of the handle 1 with an integrally formed fitment axis member 3 and a latching groove 7 provided peripherally on the fitment axis member 3.

In its centre the treatment element 2 has a plastic sleeve 4 which is stable in respect of shape and which is surrounded at all sides, that is to say with the exception of the lower open end portion of the sleeve 4, by a foam layer 5 which is several millimeters thick and which is overall of a cylindrical shape. Provided at the inside wall of the plastic sleeve 4 are latching elements 6 which, when the plastic sleeve 4 is pushed on to the fitment axis member 3, engage into and latch to the groove 7 so that the treatment element 2 is in total fixed to the fitment axis member 3 and thus also to the handle 1, while however being freely rotatable about the fitment axis member 3. It will be appreciated that the latching elements 6, 7 are only diagrammatically illustrated here and that numerous other configurations of latching elements, including those which permit external actuation, are conceivable.

As an alternative to the variant shown in FIG. 5 the treatment element, instead of an inner sleeve, could also have a shaft which projects with one end out of an end of the foam element which forms an axis connecting portion which can be inserted into a bush and preferably latched therein, which instead of the shaft or axis member in FIG. 5 is let into an end of the handle.

Referring to FIG. 6, the alternative variant wherein an axis member 3 is fixedly connected to the foam layer 5 forming the treatment surface. On the side towards the handle, the axis member 3 has a projecting corrugated connecting portion which can be inserted into a mounting bush provided in the handle 1. At least one of the axis member 3, the corrugated connecting portion, and the mounting bush has latching elements to axially fix the treatment element 2 to the handle 1 with free rotatability with respect to the handle 1.

For the purposes of the original disclosure it is pointed out that all features as can be seen by a man skilled in the art from the present description, the drawings and the appendant claims, even if they were described in specific terms only in connection with certain other features, can be combined both individually and also in any combinations with others of the features or groups of features disclosed here insofar as that has not been expressly excluded or technical aspects make such combinations impossible or meaningless. A comprehensive explicit representation of all conceivable combinations of features and emphasis of the independence of the individual features from each other is dispensed with here only for the sake of brevity and readability of the description.

The invention claimed is:

1. A device for the preventative and acute treatment of teeth and gums comprising:

an elongated handle (1) having a longitudinal axis; and a treatment element (2) mounted to a first end of the handle (1) and which is to be inserted into the mouth of a patient, said treatment element (2) having an axis of rotation (8) angled with respect to the longitudinal axis of said handle at angle of 80° to 88°, said treatment element (2) further comprising a three-dimensional, rotationally symmetrical treatment surface, wherein the treatment surface at least partially comprises an open-pore foam, and wherein the treatment element (2) is supported freely rotatably about the axis of rotation (8) in such a way that it can be rolled with its rotationally symmetrical treatment surface in the mouth of the patient along the teeth and/or gums thereof, and wherein said elongated handle includes a gripping region spaced from said first end, said handle in said gripping region having a cross-section with an outer dimension in a plane with the treatment element axis of rotation (8) and transverse to said longitudinal axis that is greater than the cross-sectional outer dimension of the handle in a plane that is transverse to the treatment element axis of rotation.

2. A device as set forth in claim 1, wherein the treatment surface comprises a substantially cylindrical surface.

3. A device as set forth in one of the claims 1-2, wherein the diameter of the treatment surface is in a range of between 5 and 20 mm.

4. A device as set forth in claim 3, wherein the diameter of the treatment surface is in a range of between 8 and 15 mm.

5. A device as set forth in one of the claims 1-2, wherein the treatment element has an inner plastic sleeve (4) which is stable in respect of shape and which can be fitted on to an axis member (3).

6. A device as set forth in claim 5, wherein at least one of the plastic sleeve (4) and the axis member (3) has latching elements to axially fix the treatment element to the handle with free rotatability with respect to the handle (1).

7. A device as set forth in one of the claims 1-2, wherein an axis member (3) is fixedly connected to a foam layer (5) forming the treatment surface and on the side towards the handle has a projecting corrugated connecting portion which can be inserted into a mounting bush provided in the handle.

8. A device as set forth in claim 7, wherein at least one of the axis member (3), the corrugated connecting portion, and the mounting bush has latching elements to axially fix the treatment element to the handle with free rotatability with respect to the handle (1).

9. A device as set forth in one of the claims 1-2, wherein the open-pore foam layer (5) of the treatment surface is of a thickness of at least 1 mm.

10. A device as set forth in claim 6, wherein the open-pore foam layer (5) of the treatment surface is of a thickness of at least 2 mm.

11. A device as set forth in one of the claims 1-2, wherein the open-pore foam of the treatment surface comprises a permanently elastic material.

12. A device as set forth in one of the claims 1-2, wherein the open-pore foam has a porosity defined as the ratio of the pore volume to the overall volume of the foam of at least 80%.

13. A device as set forth in claim 12, wherein the foam has a porosity defined as the ratio of the pore volume to the overall volume of the foam of at least 90%.

14. A device as set forth in one of the claims 1-2, wherein the mean pore size of the foam is between 0.1 and 1 mm.

15. A device as set forth in claim 14, wherein the mean pore size of the foam is between 0.2 and 0.5 mm.

* * * * *

UNITED STATES PATENT AND TRADEMARK OFFICE
CERTIFICATE OF CORRECTION

| | | |
|---|---|---|
| PATENT NO. | : 9,271,815 B2 | Page 1 of 1 |
| APPLICATION NO. | : 13/811449 | |
| DATED | : March 1, 2016 | |
| INVENTOR(S) | : Dieter Götte | |

It is certified that error appears in the above-identified patent and that said Letters Patent is hereby corrected as shown below:

Claims

Column 8, Line 35, claim 10, change "claim 6" to --- claim 8 ---

Signed and Sealed this
Third Day of May, 2016

Michelle K. Lee
*Director of the United States Patent and Trademark Office*